US00PP28342P3

(12) United States Plant Patent
Barbour

(10) Patent No.: US PP28,342 P3
(45) Date of Patent: Aug. 29, 2017

(54) OAK TREE NAMED 'GREEN NOVA'

(50) Latin Name: *Quercus bicolor*
Varietal Denomination: Green Nova

(71) Applicant: John Barbour, Hawkinsville, GA (US)

(72) Inventor: John Barbour, Hawkinsville, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 58 days.

(21) Appl. No.: 14/545,865

(22) Filed: Jun. 30, 2015

(65) Prior Publication Data

US 2017/0006749 P1 Jan. 5, 2017

(51) Int. Cl.
*A01H 5/00* (2006.01)

(52) U.S. Cl.
USPC ..... Plt./225

(58) Field of Classification Search
USPC ..... Plt./225
See application file for complete search history.

*Primary Examiner* — June Hwu
(74) *Attorney, Agent, or Firm* — C. A. Whealy

(57) ABSTRACT

A new and distinct cultivar of Oak tree named 'Green Nova', characterized by its upright pyramidal oval tree form with sturdy broad branch orientation angles; vigorous growth habit; freely branching habit with numerous lateral branches providing a full and densely foliated appearance; and glossy dark green-colored leaves that consistently abscise during the winter.

5 Drawing Sheets

Botanical designation: *Quercus bicolor.*
Cultivar denomination: 'GREEN NOVA'.

BACKGROUND OF THE INVENTION

The present invention relates to a new and distinct cultivar of Oak tree, botanically known as *Quercus bicolor*, commercially referred to as Swamp White Oak and hereinafter referred to by the name 'Green Nova'.

The new Oak tree is a product of a planned breeding program conducted by the Inventor in Pulaski and Oconee Counties, Ga. The objective of the breeding program is to create new Oak trees appropriate for urban landscapes that have a freely-branching habit with glossy dark green-colored leaves that abscise during the winter.

The new Oak tree originated from an open-pollination of an unnamed selection of *Quercus bicolor*, not patented, as the female, or seed, parent with an unknown selection of *Quercus bicolor* as the male, or pollen, parent. The new Oak tree was discovered and selected by the Inventor as a single plant from within the progeny of the stated open-pollination in a controlled environment in Pulaski County, Ga. in November, 2004.

Asexual reproduction of the new Oak tree by grafting (chip-budded during the early autumn and splice-grafted during the winter) in a controlled environment in Oconee County, Ga. has shown that the unique features of this new Oak tree are stable and reproduced true to type in successive generations.

SUMMARY OF THE INVENTION

Trees of the new Oak have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Green Nova'. These characteristics in combination distinguish 'Green Nova' as a new and distinct Oak tree:

1. Upright pyramidal oval tree form with sturdy broad branch orientation angles.
2. Vigorous growth habit.
3. Freely branching habit with numerous lateral branches providing a full and densely foliated appearance.
4. Glossy dark green-colored leaves that typically abscise during the winter.

Trees of the new Oak can be compared to trees of the female parent selection. Trees of the new Oak differ primarily from trees of the female parent selection in the following characteristics:

1. Trees of the new Oak are more freely branching than trees of the female parent selection.
2. Trees of the new Oak have a higher winter leaf abscission rate than trees of the female parent selection as more than 95% of leaves of trees of the new Oak abscise during the winter whereas only 75% of leaves of trees of the female parent selection abscise during the winter.

Trees of the new Oak can be compared to trees of *Quercus bicolor* 'Bonnie and Mike', not patented. Trees of the new Oak and 'Bonnie and Mike' differ primarily in the following characteristics:

1. Trees of the new Oak are pyramidal in shape with broad branch orientation angles whereas trees of 'Bonnie and Mike' are fastigiate in shape with narrow branch orientation angles.
2. Trees of the new Oak are more vigorous and grow 27% faster than trees of 'Bonnie and Mike'.
3. Trees of the new Oak are more freely branching than trees of 'Bonnie and Mike'.
4. Leaves of trees of the new Oak are glossier and more durable than leaves of trees of 'Bonnie and Mike'.

5. Trees of the new Oak have a higher winter leaf abscission rate than trees of 'Bonnie and Mike' as more than 95% of leaves of trees of the new Oak abscise during the winter whereas only 50% of leaves of trees of 'Bonnie and Mike' abscise during the winter.

Trees of the new Oak can also be compared to seedling selections of *Quercus bicolor* known to the Inventor, not patented. Trees of the new Oak and seedling selections of *Quercus bicolor* known to the Inventor differ primarily in the following characteristics:

1. Trees of the new Oak are more freely branching and denser than seedling selections of *Quercus bicolor* known to the Inventor.
2. Trees of the new Oak are more vigorous and grow 29% faster than seedling selections of *Quercus bicolor* known to the Inventor.
3. Trees of the new Oak are more uniform in winter leaf drop than seedling selections of *Quercus bicolor* known to the Inventor as all trees of the new Oak consistently drop their leaves during the winter whereas only 20% of the seedling selections of *Quercus bicolor* known to the Inventor drop their leaves during the winter.

BRIEF DESCRIPTION OF THE PHOTOGRAPHS

The accompanying colored photographs illustrate the overall appearance of the new Oak tree showing the colors as true as it is reasonably possible to obtain in colored reproductions of this type. Colors in the photographs may differ slightly from the color values cited in the detailed botanical description which accurately describe the colors of the new Oak tree.

The photograph on the first sheet is a side perspective view of a typical mature tree of 'Green Nova' grown during the summer in an outdoor nursery.

The photographs on the second sheet are side perspective views of typical mature trees of 'Green Nova' (left) and a seedling selection of *Quercus bicolor* known to the Inventor (right) grown during the winter in an outdoor nursery showing the differences in branch density and winter leaf abscission rate.

The photographs on the third sheet are side perspective views of typical young trees of 'Green Nova' (left) and 'Bonnie and Mike' (right) grown during the winter in an outdoor nursery showing the differences in tree shape, branch orientation angle and winter leaf abscission rate.

The photographs on the fourth sheet are close-up views of the upper surfaces of typical leaves of 'Green Nova' (left) and 'Bonnie and Mike' (right) grown during the summer in an outdoor nursery showing the differences in leaf shape and glossiness.

The photograph on the fifth sheet is a close-up view of the upper surfaces of typical leaves of 'Green Nova' (right) and 'Bonnie and Mike' (left) grown during the autumn in an outdoor nursery showing the differences in the durability of the leaves.

DETAILED BOTANICAL DESCRIPTION

The aforementioned photographs and following observations, measurements and values describe trees grown in an outdoor nursery in Pulaski County, Ga. and under cultural practices typical of commercial Oak tree production. Trees used in the photographs and description were four (referred to as "young trees") and ten (referred to as "mature trees") years old. During the production of the trees, average day temperature was 24.5° C. and average night temperature was 11.1° C. In the following description, color references are made to The Royal Horticultural Society Colour Chart, 2007 Edition, except where general terms of ordinary dictionary significance are used.

Botanical classification: *Quercus bicolor* 'Green Nova'.

Parentage:

*Female, or seed, parent*.—Unnamed selection of *Quercus bicolor*, not patented.

*Male, or pollen, parent*.—Unknown selection of *Quercus bicolor*, not patented.

Propagation:

*Type*.—By grafting scions of the new Oak tree onto an unnamed selection of *Quercus bicolor* rootstock.

Tree description:

*Tree form and growth habit*.—Deciduous tree with pyramidal tree form with broad branch orientation angles; freely branching habit with about 43 lateral branches developing per tree; full and densely-foliated appearance; vigorous growth habit; flower initiation and development have not been observed on trees of the new Oak.

*Tree height, young trees*.—About 4.11 meters.

*Tree height, mature trees*.—About 7.93 meters.

*Tree width (spread), young trees*.—About 1.68 meters.

*Tree width (spread), mature trees*.—About 4.65 meters.

*Trunk caliper, young trees*.—About 8.89 cm.

*Trunk caliper, mature trees*.—About 21.6 cm.

*Trunk bark texture*.—Flaky with elongated fissures.

*Trunk bark color*.—Ranging from between 202B and 202C, 177A, 187A and 199C; bark revealed by the fissures, close to 199B.

*Growth rate, height, young trees*.—About 1.03 meters per year.

*Growth rate, height, mature trees*.—About 79 cm per year.

*Growth rate, caliper, young and mature trees*.—About 2.2 cm per year.

*Branch angle orientation*.—Lower canopy branches, about 55° from vertical.

*Lateral branch color*.—Developing branches: Close to 199A. Mature branches: Close to between 200A tinged with close to N187A and 202A; underneath the bark, close to 199D. Immature bark texture: Smooth, glabrous.

*Mature bark texture*.—Rough, woody.

*Branch lenticels*.—New growth (one year or less): Length: About 0.5 mm to 1 mm. Diameter: About 0.5 mm to 1 mm. Shape: Round to circular. Color: Close to 199D. Older growth (three to four years): Length: About 1 mm to 3 mm. Diameter: About 0.5 mm to 1 mm. Shape: Oval to oblong. Color: Close to NN155A.

Leaf description:

*Dormant leaf buds*.—Arrangement: Terminal buds in clusters of three or more. Length: About 2.75 mm. Diameter: About 2.25 mm. Shape: Broadly ovate with rounded apices. Texture: Smooth, glabrous. Color: Close to 200B.

*Leaf arrangement*.—Alternate, simple.

*Leaf length*.—About 16.17 cm.

*Leaf width*.—About 10 cm.

*Leaf shape*.—Obovate.

*Leaf apex*.—Acute.

*Leaf base*.—Cuneate to rounded cuneate.

*Leaf margins*.—Sinuate with six to nine shallow lobes.

*Leaf venation*.—Pinnate.

*Leaf texture, upper surface*.—Smooth, glabrous; leathery.

*Leaf texture, lower surface*.—Tomentose, canescent.

*Leaf luster, upper surface*.—Very glossy.

*Leaf luster, lower surface*.—Matte.

*Leaf color*.—When developing, upper surface: Close to 137A to 137B. When developing, lower surface: Close to N138C to N138D. Fully developed, upper surface: Close to 139A; in the autumn, close to 163A to 163B; venation, close to 162A. Fully developed, lower surface: Close to 194A; in the autumn, close to 161C; venation, close to 160A.

*Winter leaf drop*.—Uniformly high leaf abscission rate; trees of the new Oak consistently drop more than 95% of their leaves during the winter.

*Leaf petioles*.—Length: About 9.53 mm. Diameter: About 2.65 mm. Texture, upper and lower surfaces: Smooth, glabrous. Color, upper surface: Close to 145C and 60A. Color, lower surface: Close to 145B and 60A.

Flowers: Flower initiation and development have not been observed on trees of the new Oak to date.

Fruits: Fruit development has not been observed on trees of the new Oak to date.

Temperature tolerance: Trees of the new Oak have been observed to tolerate high temperatures about 40.5° C. and low temperatures about −11.7° C. when grown in USDA Hardiness Zone 8.

Pathogen & pest resistance: Trees of the new Oak have been observed to have resistance to Powdery Mildew (*Microsphaera alphitoides*) and Oak Anthracnose (*Apiognomonia errabunda*).

It is claimed:

1. A new and distinct Oak tree named 'Green Nova' as illustrated and described.

* * * * *

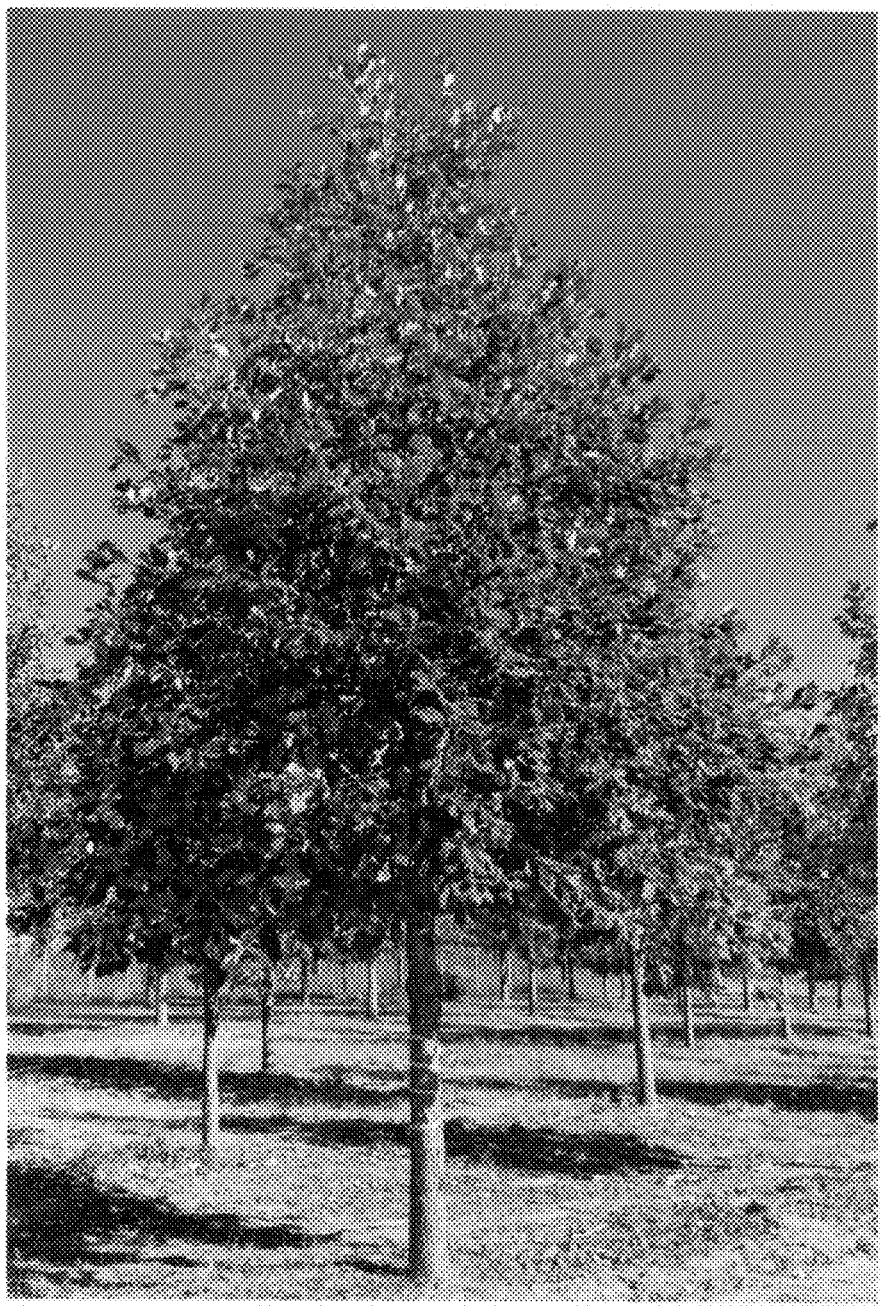

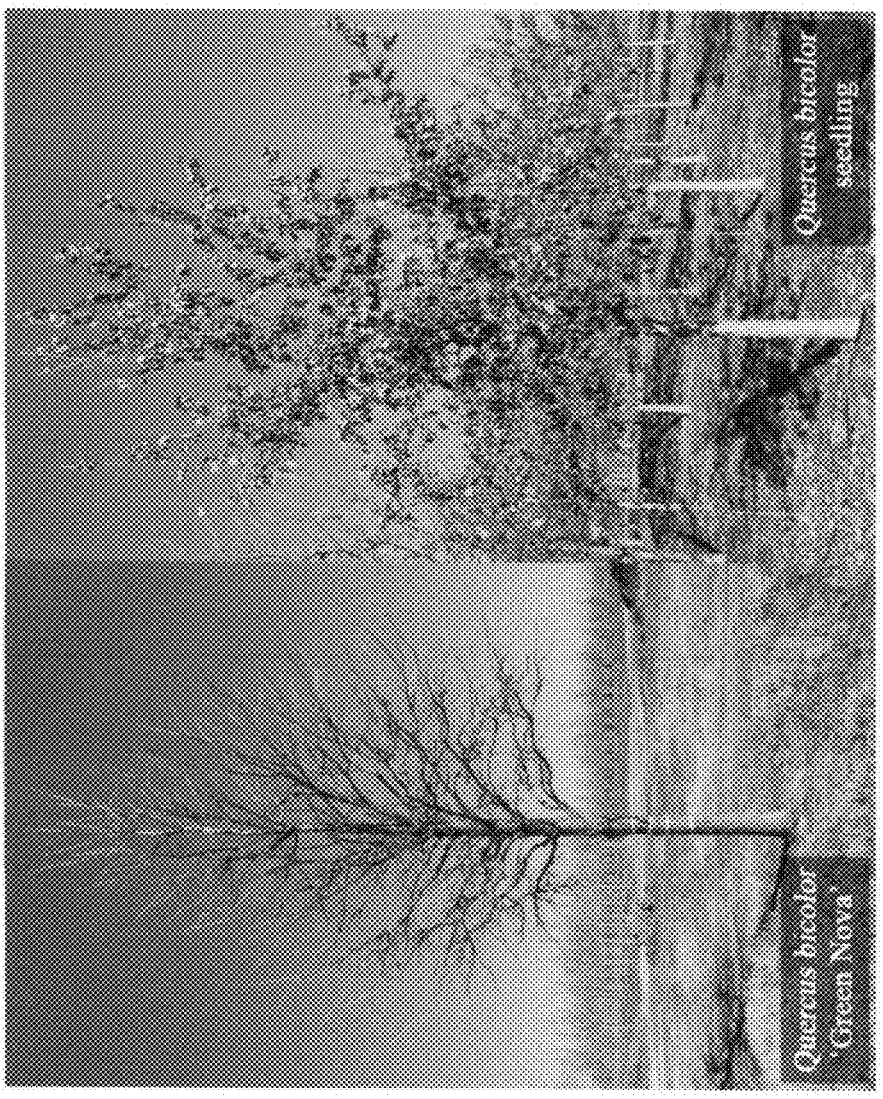
Quercus bicolor
Green Nova
Quercus bicolor
seedling

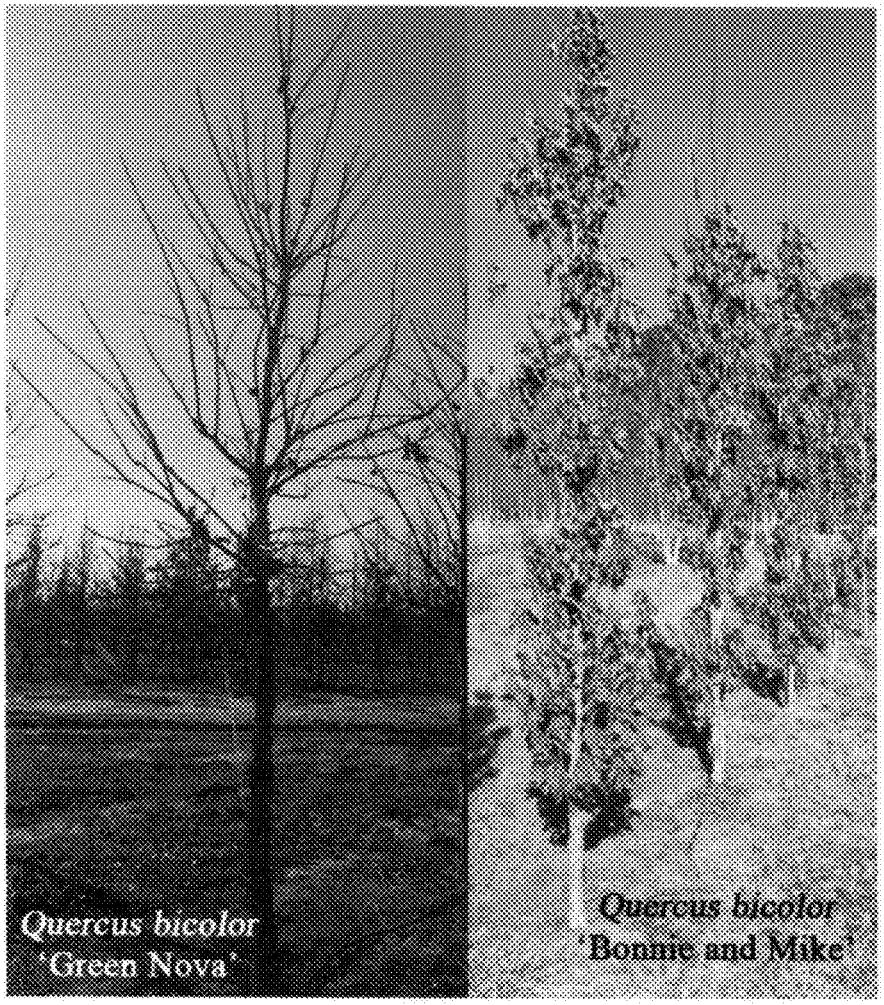
*Quercus bicolor*
'Green Nova'
*Quercus bicolor*
'Bonnie and Mike'

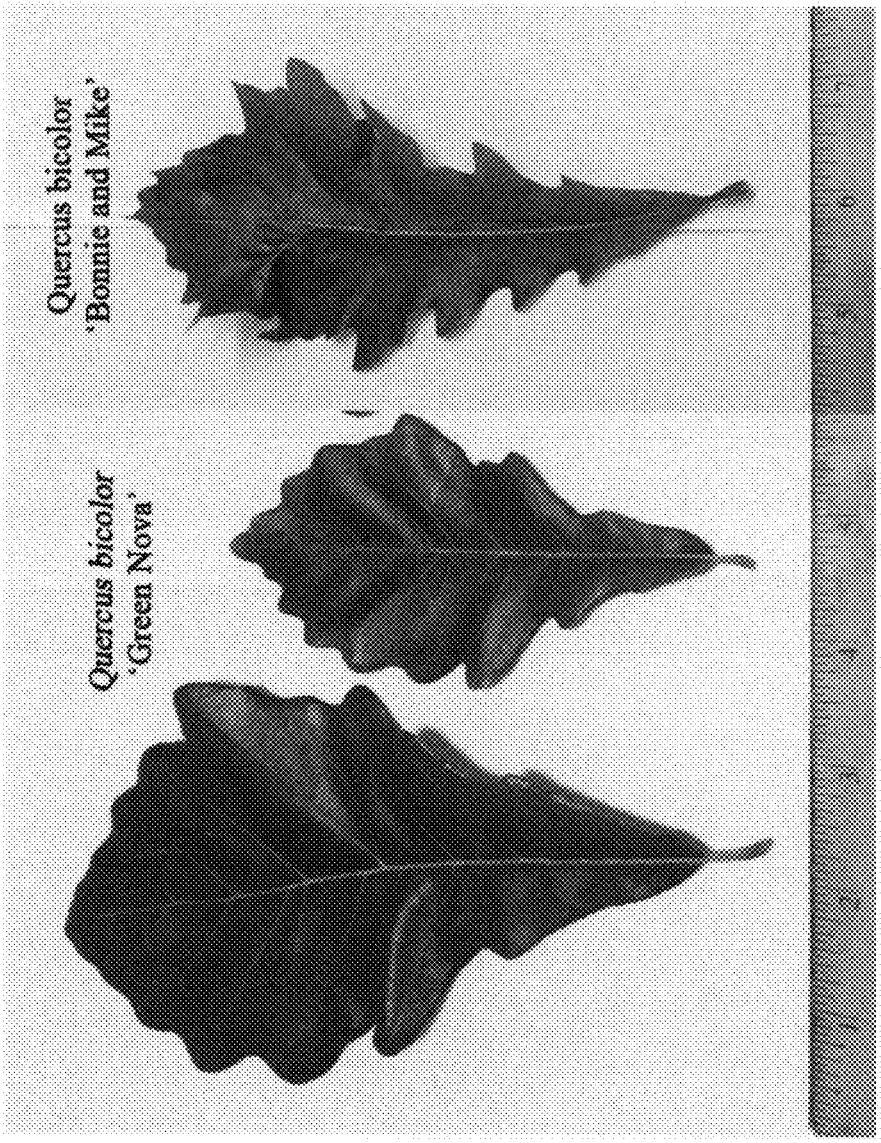
*Quercus bicolor*
'Green Nova'
*Quercus bicolor*
'Bonnie and Mike'

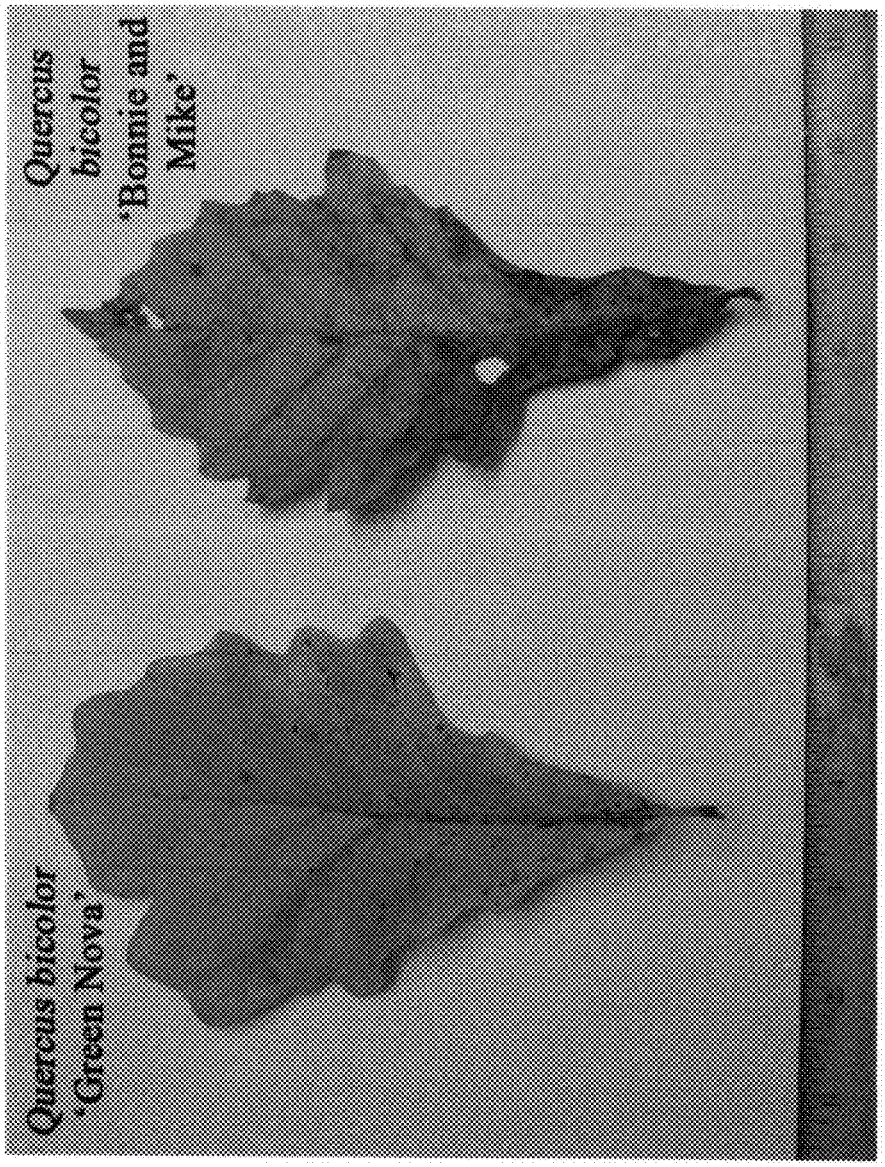
Quercus bicolor 'Green Nova'
Quercus bicolor 'Bonnie and Mike'